(12) United States Patent  
Forsberg et al.

(10) Patent No.: US 8,382,795 B2
(45) Date of Patent: Feb. 26, 2013

(54) VASCULAR PUNCTURE SEAL ANCHOR NEST

(75) Inventors: Andrew Thomas Forsberg, Minneapolis, MN (US); Loran Paprocki, St. Louis Park, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 296 days.

(21) Appl. No.: 12/548,593

(22) Filed: Aug. 27, 2009

(65) Prior Publication Data

US 2009/0312790 A1 Dec. 17, 2009

Related U.S. Application Data

(62) Division of application No. 10/726,826, filed on Dec. 3, 2003, now Pat. No. 7,597,705.

(51) Int. Cl.
*A61B 17/03* (2006.01)
(52) U.S. Cl. .......................... 606/213; 606/232
(58) Field of Classification Search .................. 606/213, 606/232
See application file for complete search history.

(56) References Cited

U.S. PATENT DOCUMENTS

| | | | |
|---|---|---|---|
| 4,317,445 A | 3/1982 | Robinson | |
| 4,852,568 A | 8/1989 | Kensey | |
| 4,890,612 A | 1/1990 | Kensey | |
| 5,021,059 A | 6/1991 | Kensey et al. | |
| 5,061,274 A | 10/1991 | Kensey | |
| 5,192,302 A | 3/1993 | Kensey et al. | |
| 5,222,974 A | 6/1993 | Kensey et al. | |
| 5,282,827 A | 2/1994 | Kensey et al. | |
| 5,290,310 A | 3/1994 | Makower et al. | |
| 5,292,332 A | 3/1994 | Lee | |
| 5,306,254 A | 4/1994 | Nash et al. | |
| 5,312,435 A | 5/1994 | Nash et al. | |
| 5,320,639 A | 6/1994 | Rudnick | |
| 5,324,306 A | 6/1994 | Makower et al. | |
| 5,326,350 A | 7/1994 | Li | |
| 5,342,393 A | 8/1994 | Stack | |
| 5,383,897 A | 1/1995 | Wholey | |
| 5,383,899 A | 1/1995 | Hammerslag | |
| RE34,866 E | 2/1995 | Kensey et al. | |
| 5,403,329 A | 4/1995 | Hinchcliffe | |
| 5,405,354 A | 4/1995 | Sarrett | |
| 5,411,520 A | 5/1995 | Nash et al. | |
| 5,431,639 A | 7/1995 | Shaw | |
| 5,431,666 A | 7/1995 | Sauer et al. | |
| 5,437,631 A | 8/1995 | Janzen | |
| 5,441,517 A * | 8/1995 | Kensey et al. ................ 606/213 |
| 5,443,481 A | 8/1995 | Lee | |
| 5,462,561 A | 10/1995 | Voda | |
| 5,486,195 A | 1/1996 | Myers et al. | |
| 5,496,332 A | 3/1996 | Sierra et al. | |
| 5,496,335 A | 3/1996 | Thomason et al. | |
| 5,507,744 A | 4/1996 | Tay et al. | |
| 5,507,758 A | 4/1996 | Thomason et al. | |
| 5,531,759 A | 7/1996 | Kensey et al. | |
| 5,534,012 A | 7/1996 | Bonutti | |
| 5,545,178 A | 8/1996 | Kensey et al. | |
| 5,571,181 A | 11/1996 | Li | |
| 5,601,603 A | 2/1997 | Illi | |
| 5,613,974 A | 3/1997 | Andreas et al. | |

(Continued)

*Primary Examiner* — Ryan Severson
(74) *Attorney, Agent, or Firm* — Holland & Hart LLP (57) ABSTRACT

The present invention provides a method and apparatus for sealing a subcutaneous tissue puncture. The method and apparatus increases the reliability of device function by creating a multi-level anchor nest in a carrier tube of a tissue puncture closure device. The multi-level nest allows an insertion sheath or other deployment member to slide between the carrier tube and the anchor to rotate and deploy the anchor within an artery or other lumen.

30 Claims, 12 Drawing Sheets

U.S. PATENT DOCUMENTS

| | | | |
|---|---|---|---|
| 5,626,588 A | 5/1997 | Sauer et al. | |
| 5,643,318 A | 7/1997 | Tsukernik et al. | |
| 5,645,566 A | 7/1997 | Brenneman et al. | |
| 5,649,959 A | 7/1997 | Hannam et al. | |
| 5,662,663 A | 9/1997 | Shallman | |
| 5,662,681 A * | 9/1997 | Nash et al. | 606/213 |
| 5,665,107 A | 9/1997 | Hammerslag | |
| 5,674,231 A | 10/1997 | Green et al. | |
| 5,700,277 A | 12/1997 | Nash et al. | |
| 5,716,375 A | 2/1998 | Fowler | |
| 5,718,717 A | 2/1998 | Bonutti | |
| 5,725,551 A | 3/1998 | Myers et al. | |
| 5,728,114 A | 3/1998 | Evans et al. | |
| 5,728,122 A | 3/1998 | Leschinsky et al. | |
| 5,728,132 A | 3/1998 | Van Tassel et al. | |
| 5,728,134 A | 3/1998 | Barak | |
| 5,741,223 A | 4/1998 | Janzen et al. | |
| 5,755,727 A | 5/1998 | Kontos | |
| 5,759,194 A | 6/1998 | Hammerslag | |
| 5,766,183 A | 6/1998 | Sauer | |
| 5,766,206 A | 6/1998 | Wijkamp et al. | |
| 5,779,719 A | 7/1998 | Klein et al. | |
| 5,792,173 A | 8/1998 | Breen et al. | |
| 5,810,810 A | 9/1998 | Tay et al. | |
| 5,810,846 A | 9/1998 | Virnich et al. | |
| 5,810,850 A | 9/1998 | Hathaway et al. | |
| 5,810,884 A | 9/1998 | Kim | |
| 5,814,065 A | 9/1998 | Diaz | |
| 5,814,073 A * | 9/1998 | Bonutti | 606/232 |
| 5,820,631 A | 10/1998 | Nobles | |
| 5,843,124 A | 12/1998 | Hammerslag | |
| 5,853,421 A | 12/1998 | Leschinsky et al. | |
| 5,855,585 A | 1/1999 | Kontos | |
| 5,860,990 A | 1/1999 | Nobles et al. | |
| 5,860,991 A | 1/1999 | Klein et al. | |
| 5,861,004 A | 1/1999 | Kensey et al. | |
| 5,868,762 A | 2/1999 | Cragg et al. | |
| 5,868,778 A | 2/1999 | Gershony et al. | |
| 5,876,411 A | 3/1999 | Kontos | |
| 5,906,631 A | 5/1999 | Imran | |
| 5,910,155 A | 6/1999 | Ratcliff et al. | |
| 5,916,236 A | 6/1999 | Muijs Van de Moer et al. | |
| 5,919,207 A | 7/1999 | Taheri | |
| 5,921,994 A | 7/1999 | Andreas et al. | |
| 5,928,266 A | 7/1999 | Kontos | |
| 5,941,897 A | 8/1999 | Myers | |
| 5,948,425 A | 9/1999 | Janzen et al. | |
| 5,964,782 A | 10/1999 | Lafontaine et al. | |
| 5,976,161 A | 11/1999 | Kirsch et al. | |
| 5,980,539 A | 11/1999 | Kontos | |
| 5,984,950 A | 11/1999 | Cragg et al. | |
| 5,997,555 A | 12/1999 | Kontos | |
| 6,001,109 A | 12/1999 | Kontos | |
| 6,007,562 A | 12/1999 | Harren et al. | |
| 6,017,359 A | 1/2000 | Gershony et al. | |
| 6,022,372 A | 2/2000 | Kontos | |
| 6,024,747 A | 2/2000 | Kontos | |
| 6,033,401 A | 3/2000 | Edwards et al. | |
| 6,033,427 A | 3/2000 | Lee | |
| 6,036,721 A | 3/2000 | Harren et al. | |
| 6,042,601 A | 3/2000 | Smith | |
| 6,045,569 A | 4/2000 | Kensey et al. | |
| 6,048,357 A | 4/2000 | Kontos | |
| 6,048,358 A | 4/2000 | Barak | |
| 6,063,085 A | 5/2000 | Tay et al. | |
| 6,071,300 A | 6/2000 | Brenneman et al. | |
| 6,077,276 A | 6/2000 | Kontos | |
| 6,077,279 A | 6/2000 | Kontos | |
| 6,110,184 A | 8/2000 | Weadock | |
| 6,117,145 A | 9/2000 | Wood et al. | |
| 6,120,524 A | 9/2000 | Taheri | |
| 6,126,675 A | 10/2000 | Shchervinsky et al. | |
| 6,136,010 A | 10/2000 | Modesitt et al. | |
| 6,139,556 A | 10/2000 | Kontos | |
| 6,162,192 A | 12/2000 | Cragg et al. | |
| 6,174,322 B1 | 1/2001 | Schneidt | |
| 6,179,863 B1 | 1/2001 | Kensey et al. | |
| 6,183,485 B1 | 2/2001 | Thomason et al. | |
| 6,183,496 B1 | 2/2001 | Urbanski | |
| 6,190,400 B1 | 2/2001 | Van De Moer et al. | |
| 6,197,042 B1 | 3/2001 | Ginn et al. | |
| 6,206,893 B1 | 3/2001 | Klein et al. | |
| 6,231,561 B1 | 5/2001 | Frazier et al. | |
| 6,425,911 B1 | 7/2002 | Akerfeldt et al. | |
| 6,451,030 B2 | 9/2002 | Li et al. | |
| 6,508,828 B1 | 1/2003 | Akerfeldt et al. | |
| 6,547,806 B1 | 4/2003 | Ding | |
| 6,569,185 B2 | 5/2003 | Ungs | |
| 6,596,014 B2 | 7/2003 | Levinson et al. | |
| 6,682,489 B2 | 1/2004 | Tenerz et al. | |
| 6,712,837 B2 | 3/2004 | Akerfeldt et al. | |
| 6,786,915 B2 | 9/2004 | Akerfeldt et al. | |
| 6,860,895 B1 | 3/2005 | Akerfeldt et al. | |
| 2001/0002440 A1 * | 5/2001 | Bonutti | 606/232 |

* cited by examiner

Fig. 1A
(Conventional)

Fig. 1B
(Conventional)

Fig. 2A
(Conventional)

Fig. 2B
(Conventional)

Fig. 3
(Conventional)

Fig. 4
(Conventional)

Fig. 5
(Conventional)

Fig. 6
(Conventional)

VASCULAR PUNCTURE SEAL ANCHOR NEST

RELATED APPLICATION

This is a division of U.S. patent application Ser. No. 10/726,826 filed on 3 Dec. 2003, now issued as U.S. Pat. No. 7,597,705, the disclosure of which is incorporated, in its entirety, by this reference.

FIELD OF THE INVENTION

The present invention relates to medical devices, and, more particularly, to a vascular puncture sealing apparatus with nest features to aid in anchor function.

BACKGROUND OF THE INVENTION

Various medical procedures, particularly cardiology procedures, involve accessing a corporeal vessel or other lumen through a percutaneous sheath. Insertion of the sheath necessarily requires a hole or opening in the vessel wall so that a medical procedure can be performed through the sheath. After the particular medical procedure has been performed, the sheath must eventually be removed from the vessel and the access hole in the vessel wall must be closed.

A number of prior vascular closure devices have been developed to close the hole or puncture in the vessel wall. Closing the hole typically involves packing a resorbable sealing plug at the hole or sandwiching the hole between the sealing plug and an anchor. Examples of prior vascular closure devices are described in U.S. Pat. Nos. 6,179,863; 6,090,130; and 6,045,569 and related patents that are hereby incorporated by reference.

Placing the sealing plug often comprises several steps. First, a puncture site is located. A puncture locator is placed in and through the insertion sheath such that an inlet port in the puncture locator resides outside a distal end of the insertion sheath a predetermined distance. The insertion sheath and puncture locator are inserted through the puncture into a blood vessel. As the distal end of the puncture locator penetrates the blood vessel, blood flows into the inlet port and out of a drip hole via a flow path through the puncture locator.

Blood exiting the drip hole indicates that the puncture locator and insertion sheath have just penetrated the blood vessel. To ensure proper placement of the insertion sheath and subsequently the closure device, the insertion sheath and puncture locator are normally backed out of the vessel until blood stops flowing from the drip hole. Next, the insertion sheath and puncture locator are re-inserted into the blood vessel until blood starts flowing again from the drip hole. Proper depth of penetration and location of the assembly is established by continuing to insert an additional predetermined distance, for example, an operator often inserts the assembly 1 to 2 centimeters further if the blood vessel is a femoral artery. Once the insertion sheath is properly located, the puncture locator is removed and the vascular closure device may be inserted through the sheath and into to the blood vessel.

An anchor at a distal end of the vascular closure device is then deployed within the artery. The anchor is initially aligned with a longitudinal axis of the closure device in a covered nest of the closure device. The anchor is deployed by removing a cover from the anchor and inserting the anchor through the insertion sheath, which allows the anchor to rotate and align itself with an interior wall of the blood vessel. However, sometimes when the anchor is deployed, it tends to remain in or reenter the sheath instead of rotating and aligning with the blood vessel. This phenomenon is termed "shuttling." Shuttling disables the function, and negates the benefit, of the device. Therefore, it is desirable to have an apparatus that reduces or eliminates anchor shuttle so that the closure device will function as expected.

SUMMARY OF THE INVENTION

In one of many possible embodiments, the present invention provides a tissue puncture closure assembly comprising a closure device for partial insertion into and sealing of an internal tissue wall puncture. The closure device includes a filament extending from a first end of the closure device, a nest comprising a first surface, an anchor for insertion through the tissue wall puncture seated in the nest and attached to the filament at the first end of the closure device, a sealing plug slidingly attached to the filament adjacent to the anchor, and a gap between the nest and a portion of the anchor. The nest may include a second surface spaced from a first surface of the anchor, the spacing between the first surface of the anchor and the second surface of the nest defining the gap. The first and second nest surfaces may be approximately parallel to one another. The nest may also include a third surface, where the first, second and third nest surfaces are compressed to different depths. The assembly may also include an insertion sheath that has a first end and is receptive of the closure device. The first end of the insertion sheath may include a monofold that fits in the gap between the nest and the anchor upon distal movement of the insertion sheath relative to the closure device. Alternatively, the anchor may include an indentation spaced from the first surface of the nest, the spacing between the indentation in the anchor and the first surface of the nest defining the gap.

In another embodiment the invention provides a tissue puncture closure assembly comprising another closure device for partial insertion into and sealing of an internal tissue wall puncture. The closure device includes a carrier tube having a split-level nest at a distal end, a filament extending through the carrier tube, and an anchor attached to the filament at the distal end of the carrier tube and seated in the split-level nest. The closure device may further include a sealing plug disposed inside the distal end of the carrier tube. The sealing plug is slidingly attached to the filament. The split-level nest may include a first nest surface adjacent to a first surface of the anchor, and a second nest surface spaced from the first surface of the anchor. The split-level nest may be a tri-level nest.

Another embodiment of the invention provides a tissue puncture closure device, the tissue puncture closure device comprising a carrier tube having a distal end, a sealing plug disposed inside the distal end of the carrier tube, a multi-level compression zone or area disposed in the distal end of the carrier, and an anchor seated in the multi-level compression area of the carrier. The multi-level compression area comprises a first compression zone at a first depth, and a second compression zone at a second depth, such that the anchor bears against the first compression zone and a first gap is formed between the anchor and the second compression zone. The multi-level compression zone may include a third compression zone at a third depth, such that a second gap larger than the first gap is formed between the anchor and the third compression zone.

Another embodiment of the invention provides a tissue puncture closure device assembly including a carrier tube having a distal end and a filament extending therethrough, a sealing plug disposed inside the distal end of the carrier tube and attached to the filament, an anchor attached to the filament at the distal end of the carrier tube, and a multi-level die for compressing a multi-level nest in the distal end of the carrier tube. The multi-level die includes a first level and a second level, the second level being higher than the first level. The multi-level die may include a third level, the third level being higher than the first and second levels.

Another aspect of invention provides a method of making a tissue puncture closure device including providing a carrier tube, threading a suture through the carrier tube, threading the suture through a sealing plug and an anchor, and crushing a multi-level nest into a distal end of the carrier tube. The method may also include nesting the anchor in the multi-level nest. The nesting may further comprise leaving a gap between a portion of the anchor and one level of the multi-level nest. The compression of the carrier tube may include engaging a multi-level die with the distal end of the carrier tube. The multi-level nest may include two or more different levels.

Another aspect of the invention provides a method of sealing a tissue puncture in an internal tissue wall accessible through a percutaneous incision. The method includes providing a tissue puncture closure device comprising a carrier tube with a filament extending therethrough. The filament is connected at a distal end of the carrier tube to an anchor, and the anchor is seated in a multi-level nest disposed in the carrier tube. The filament is also connected to a sealing plug located proximal of the anchor for disposition and anchoring about the tissue puncture. The method also includes inserting the tissue puncture closure device into the percutaneous incision, deploying the anchor into the tissue puncture, withdrawing the closure device from the percutaneous incision, and tamping the sealing plug toward the anchor. The step of deploying the anchor may further comprise sliding a formed monofold tip of an insertion sheath into a gap formed between the anchor and the multi-level nest disposed in the carrier tube.

Another aspect of the invention provides a method of reducing anchor shuttle in a subcutaneous tissue puncture scaling device comprising providing a gap between a carrier tube of the tissue puncture sealing device and the anchor by creating a multi-level nest in the carrier tube, where the anchor initially seats in the multi-level nest.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical elements.

DETAILED DESCRIPTION

As mentioned above, vascular procedures are commonly performed throughout the world and require access to a lumen through a puncture. Most often, the lumen is a femoral artery. To close the puncture, many times a closure device is used to sandwich the puncture between an anchor and a sealing plug. However, there exists a possibility for the anchor to not deploy, disabling the function and negating the benefit of the device. The present invention describes methods and apparatus to reduce or eliminate non-deployment or "shuttle" of a closure device anchor. While the vascular instruments shown and described below include insertion sheaths and puncture sealing devices, the application of principles described herein to reduce anchor shuttle is not limited to the specific devices shown. The principles described herein may be used to reduce anchor shuttle for any vascular closure device. Therefore, while the description below is directed primarily to arterial procedures and certain embodiments of a vascular closure device, the methods and apparatus are only limited by the appended claims.

As used throughout the claims and specification the term "monofold" is used broadly to encompass any plastic deformation of a tube tip, especially a plastically deformed tube tip that forms a one-way valve with respect to an anchor. The term "approximately" or "substantially" means within ten percent of a given measurement or property. A "lumen" refers to any open space or cavity in a bodily organ, especially in a blood vessel. The words "including" and "having," as used in the specification, including the claims, have the same meaning as the word "comprising."

Figure 1A:
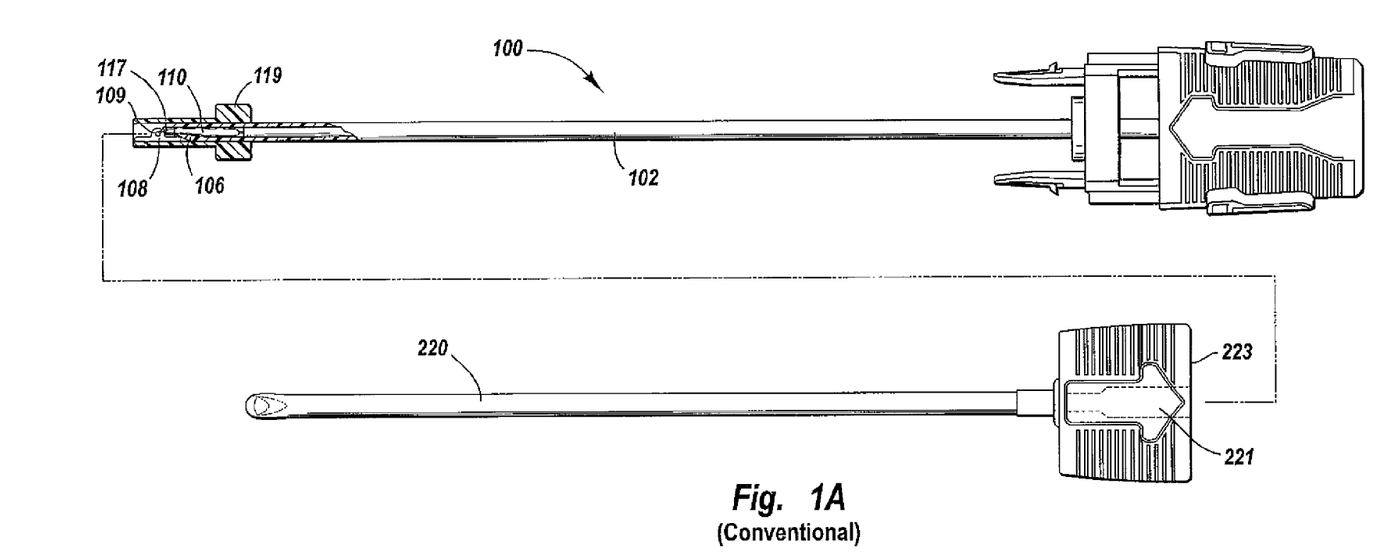
FIG. 1A is a cut-away view of a tissue puncture closure device according to the prior art.
Figure 1B:
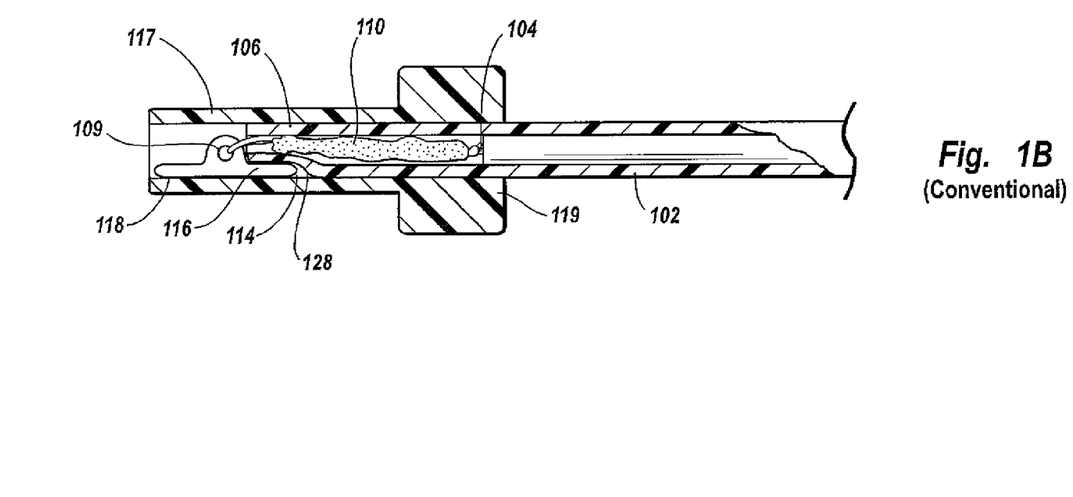
FIG. 1B is a detail of the cut-away section of FIG. 1A.

Referring now to the drawings, and in particular to FIGS. 1A-1B, a vascular puncture closure device 100 is shown according to the prior art. The vascular puncture closure device 100 includes a carrier tube 102 with a filament or suture 104 extending at least partially therethrough. External to the first or distal end 106 of the carrier tube is an anchor 108. The anchor is an elongated, stiff, low profile member including an eye 109 formed at the middle. The anchor 108 is typically made of a biologically resorbable polymer.

The suture 104 is treaded through the anchor 108 and back to a collagen sponge 110. The collagen sponge 110 is slidingly attached to the suture 104 as the suture passes distally through the carrier tube 102, but as the suture traverses the anchor 108 and reenters the carrier tube 102, it is securely slip knotted proximal to the collagen sponge 110 to facilitate cinching of the collagen sponge 110 when the closure device 100 is properly placed and the anchor 108 deployed (see FIG. 5).

The carrier tube includes a tamping tube 112 disposed therein. The tamping tube 112 is slidingly mounted on the suture 104 and may be used by an operator to tamp the collagen sponge 110 toward the anchor 108 at an appropriate time to plug a percutaneous tissue puncture.

At the distal end 106 of the carrier tube 102 is a nest 114. Prior to deployment of the anchor 108 within an artery, the eye 109 rests outside the distal end 106 of the carrier tube 102, and one end 116 of the anchor 108 rests in the nest 114. The nest 114 is typically compressed or crushed to a depth such that a second surface 118 of the anchor 108 is flush with the outer diameter of the carrier tube 102. The nest 114 is compressed to a length that is longer than the end 116 of the anchor 108. The anchor 108 may be temporarily held in place in the nest 114 by a bypass tube 117 disposed over the distal end 106 of the carrier tube 102.

Figure 2A:
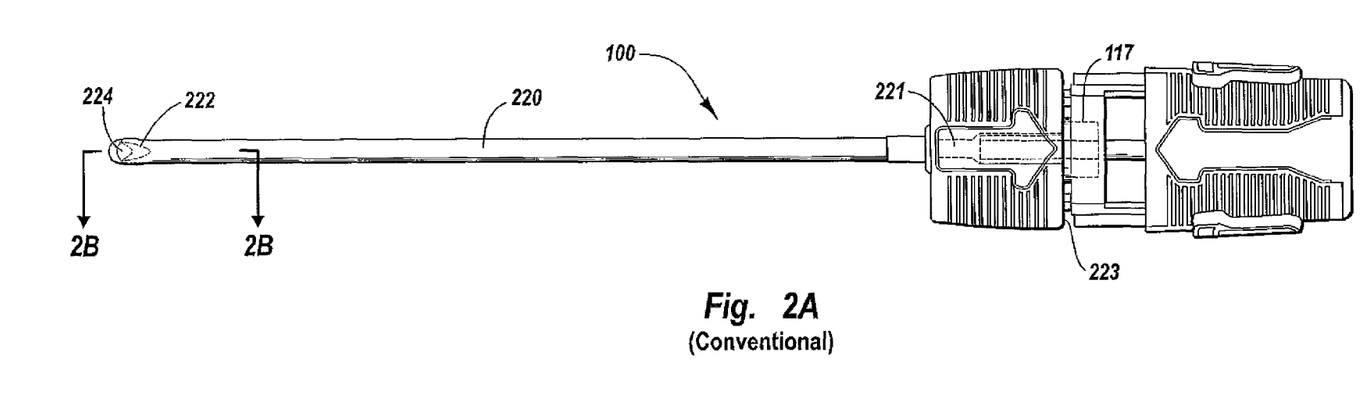
FIG. 2A is a top view of the tissue puncture closure device of FIG. 1A engaged with an insertion sheath in a first position according to the prior art.
Figure 2B:
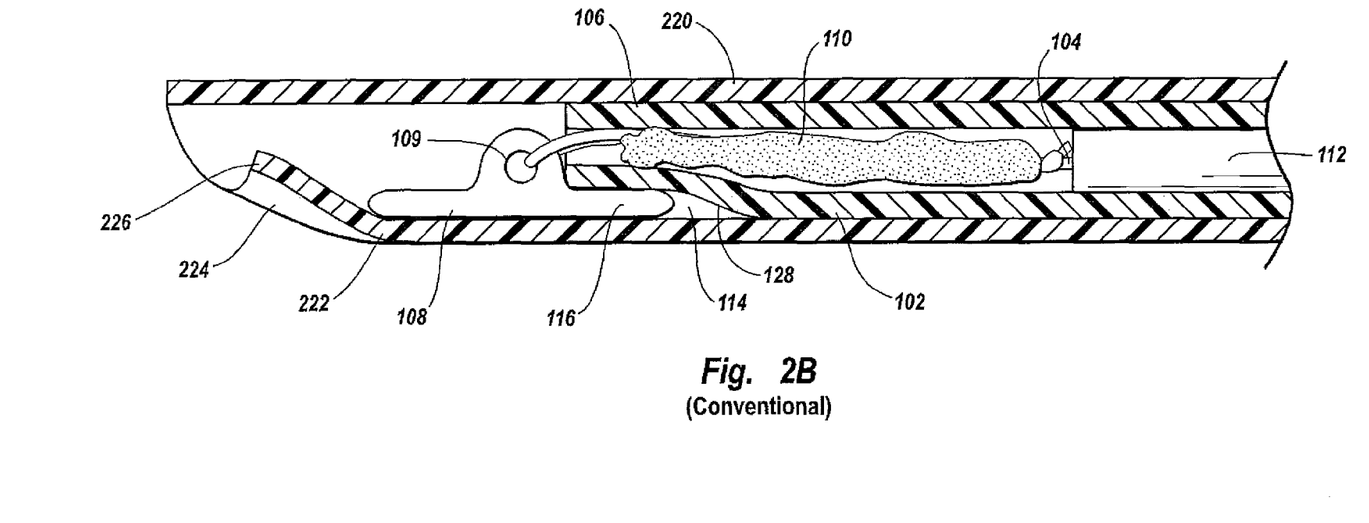
FIG. 2B is a detailed cross-sectional view of the tissue puncture closure device and insertion sheath of FIG. 2A.
Figure 5:
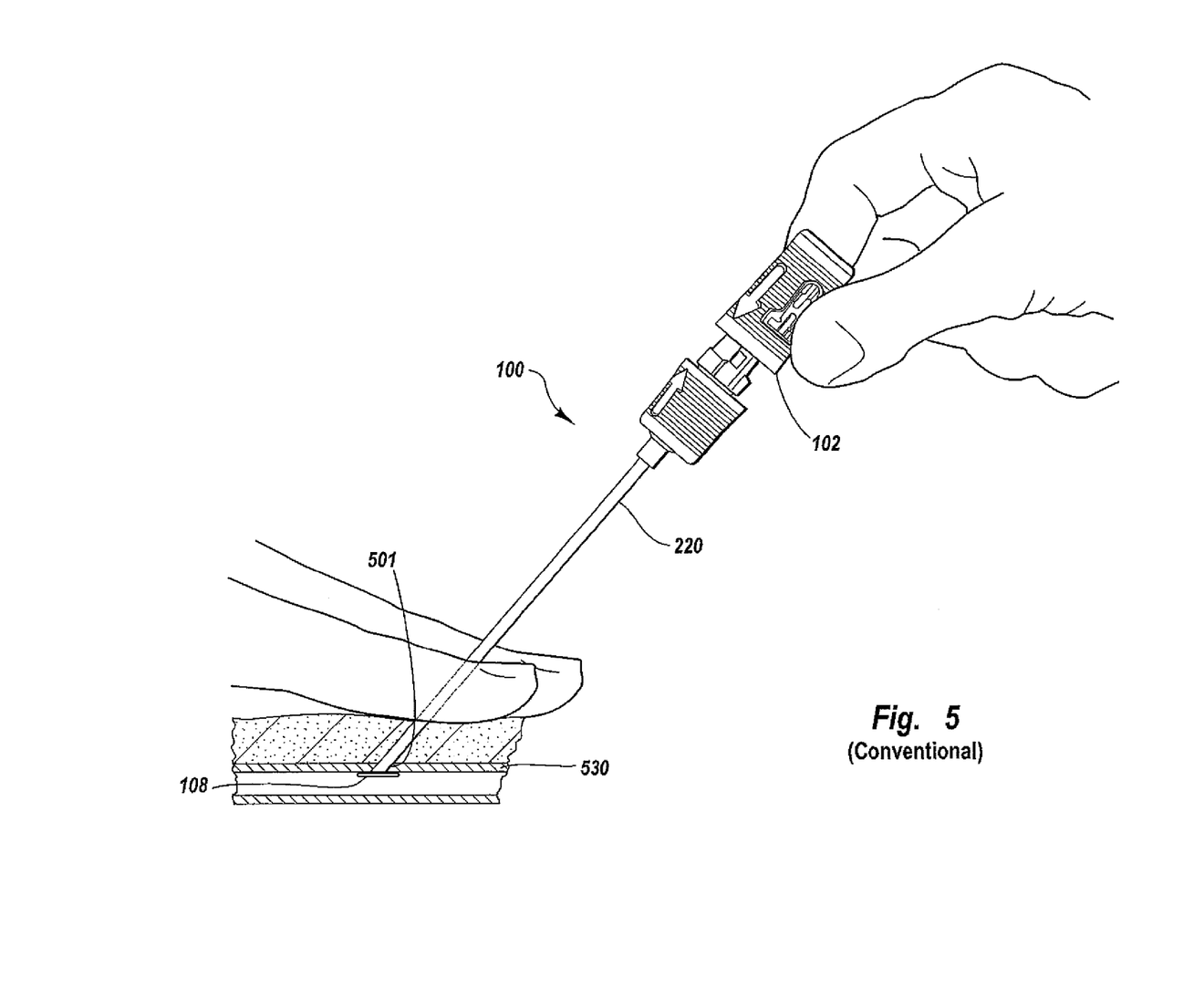
FIG. 5 is a perspective view of the tissue puncture closure device of FIG. 1A and insertion sheath of FIG. 2A shown in relation to a patient with an anchor deployed according to the prior art.

The flush arrangement of the anchor 108 and carrier tube 102 allows the anchor to be inserted into an insertion sheath 220 as shown in FIGS. 2A-2B, and eventually through an arterial puncture 501 (shown in FIG. 5). However, the bypass tube 117 includes an oversized head 119 that prevents the bypass tube 117 from passing through an internal passage 221 of the insertion sheath 220. Therefore, as the puncture closure device 100 is inserted into the internal passage 221 of the insertion sheath 220, the oversized head 119 bears against a surface 223 of insertion sheath. Further insertion of the puncture closure device 100 results in sliding movement between the carrier tube 102 and the bypass tube 117, releasing the anchor 108 from the bypass tube 117. However, the anchor 108 remains in the nest 114 following release from the bypass tube 117, limited in movement by the insertion sheath 220.

Figure 3:
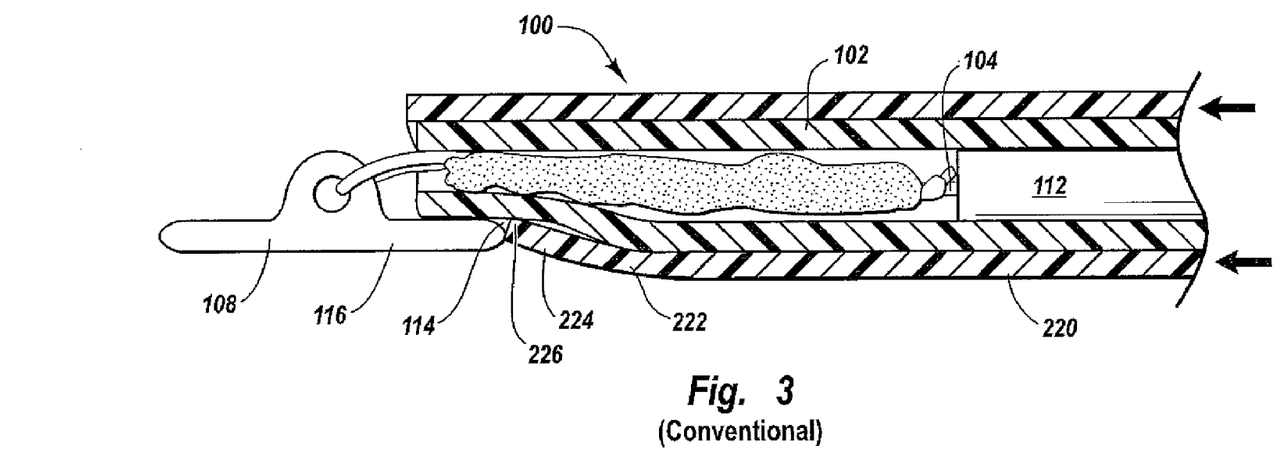
FIG. 3 is a cross-sectional view of the tissue puncture closure device of FIG. 1A in relation to the insertion sheath of FIG. 2A in a second position according to the prior art.

The insertion sheath 220 includes a first end 222 having a monofold 224. The monofold 224 acts as a one-way valve to the anchor 108. As shown in FIGS. 2A-2B and 3, the monofold 224 is a plastic deformation in a portion of the insertion sheath 220 that elastically flexes as the anchor 108 is pushed out through the first end 222 of the insertion sheath 220. However, as the anchor 108 passes though and out of the first end 222 of the insertion sheath 220 as shown in FIG. 3, the monofold 224 attempts to spring back to its original deformed position and a biased tip 226 of the monofold 224 engages the nest 114. As relative movement between the carrier tube 102 and the insertion sheath 220 continues, the biased tip 226 traverses the contour 128 of the carrier tube nest 114 in a proximal direction.

Figure 4:
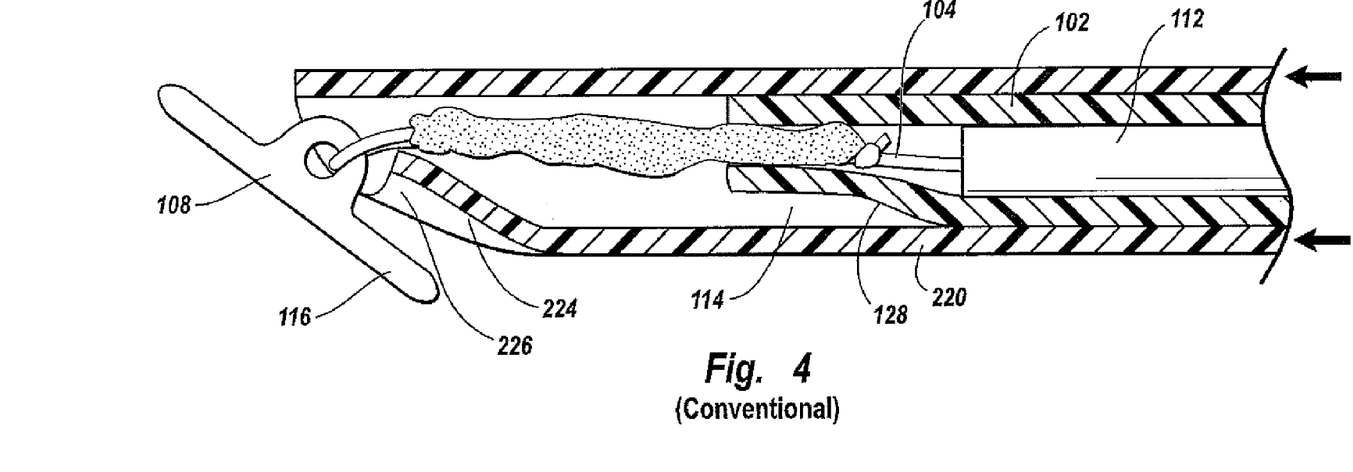
FIG. 4 is a cross-sectional view of the tissue puncture closure devices of FIG. 1A in relation to the insertion sheath of FIG. 2A in a third position according to the prior art.

Typically, after the anchor 108 passes through the first end 222 of the insertion sheath 220 and enters an artery 530 (FIG. 5), the puncture closure device 100 is pulled in a proximal direction with respect to the insertion sheath 220. The biased tip 226 of the monofold 224 thus follows the contour 128 and usually slides distally between the anchor 108 and the nest 114, causing the anchor to rotate as shown in FIG. 4. Accordingly, if all goes well, the anchor 108 is deployed within the artery as shown in FIG. 5 and does not reenter the insertion sheath 220.

Figure 6:
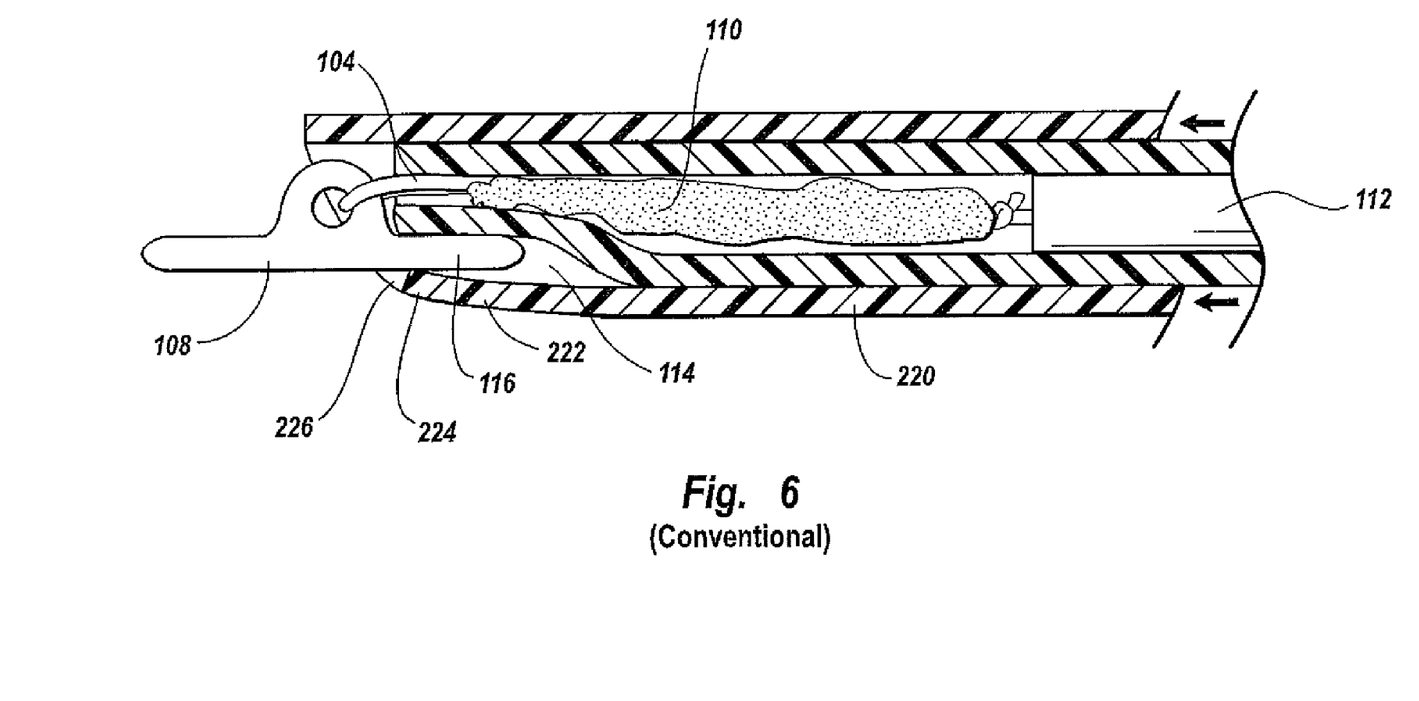
FIG. 6 is a cross-sectional view of the tissue puncture closure device of FIG. 1A in relation to the insertion sheath of FIG. 2A in a fourth position illustrating shuttling according to the prior art.

However, because the end 116 of the anchor 108 normally bears directly against the nest 114, sometimes the biased tip 226 of the monofold 224 slides over the anchor 108 as shown in FIG. 6 when the closure device 100 is pulled proximally with respect to the insertion sheath 220 instead of sliding between the end 116 and nest 114. Thus, rather than deploying properly within the artery, the anchor 108 is sometimes reinserted into the insertion sheath 220, and the puncture closure device 100 fails.

Figure 7:
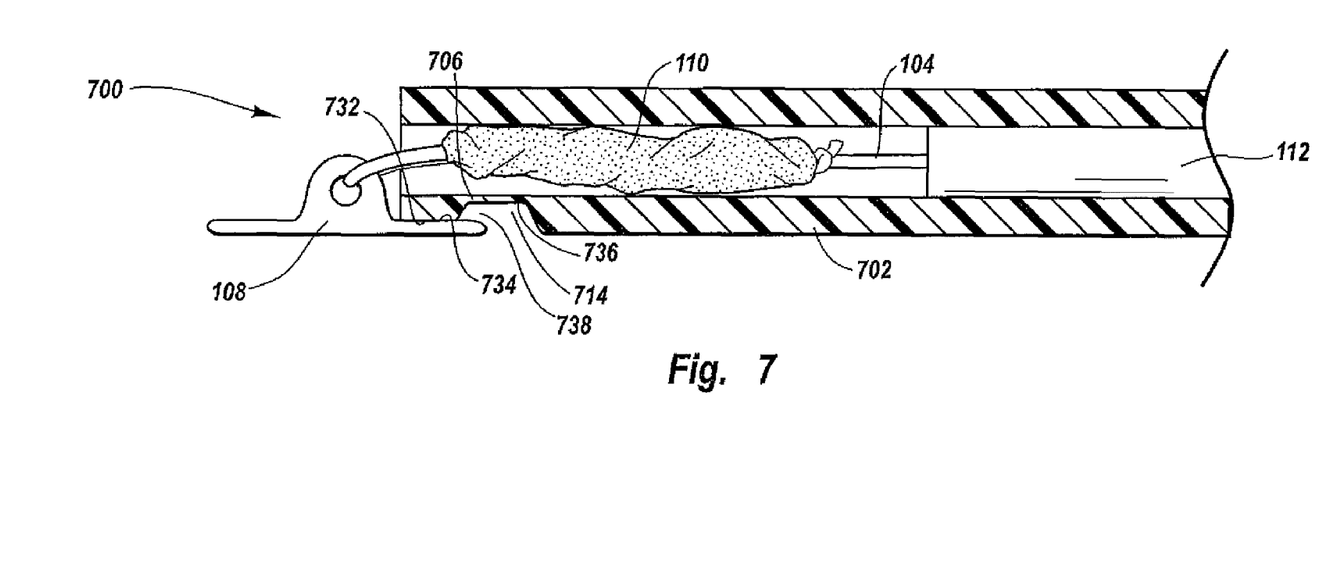
FIG. 7 is a cross-sectional view of a tissue puncture closure device according to one embodiment of the present invention.

Therefore, according to some embodiments of the present invention, a tissue closure device 700 includes a modified carrier tube 702 as shown in FIG. 7. The modified carrier tube 702 includes a split-level or multi-level nest 714 at the first or distal end 706. When the anchor is seated in a first or insertion position as shown, the multi-level nest 714 of FIG. 7 includes a first surface 732 that is adjacent to a first surface 734 of the anchor 108. The first surface 734 is facing radially inward. However, the multi-level nest also includes a second surface 736 that is spaced from the first surface 734 of the anchor 108, creating a gap 738 between a portion of the end 116 of the anchor 108 and the second surface 736 of the nest 714. The first and second surfaces 732, 736 are substantially parallel to one another as shown, but this is not necessarily so. The second surface 736 is positioned proximal of the first surface 732 of the multi-level nest 714. The second surface 736 is facing the first surface 734 in a radially outward direction.

Figure 8:
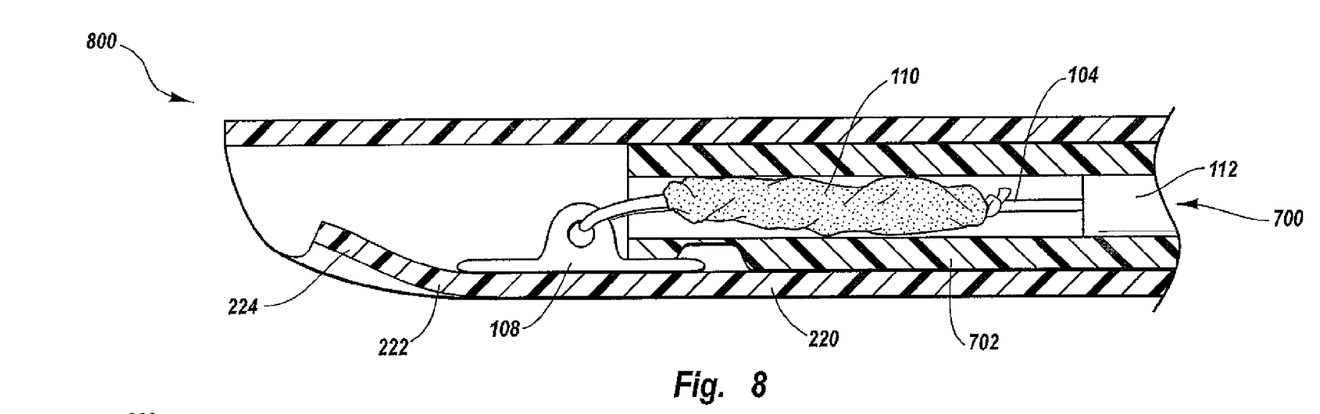
FIG. 8 is a cross-sectional view of the tissue puncture closure device of FIG. 7 shown in relation to an insertion sheath in a first position according to one embodiment of the present invention.
Figure 9:
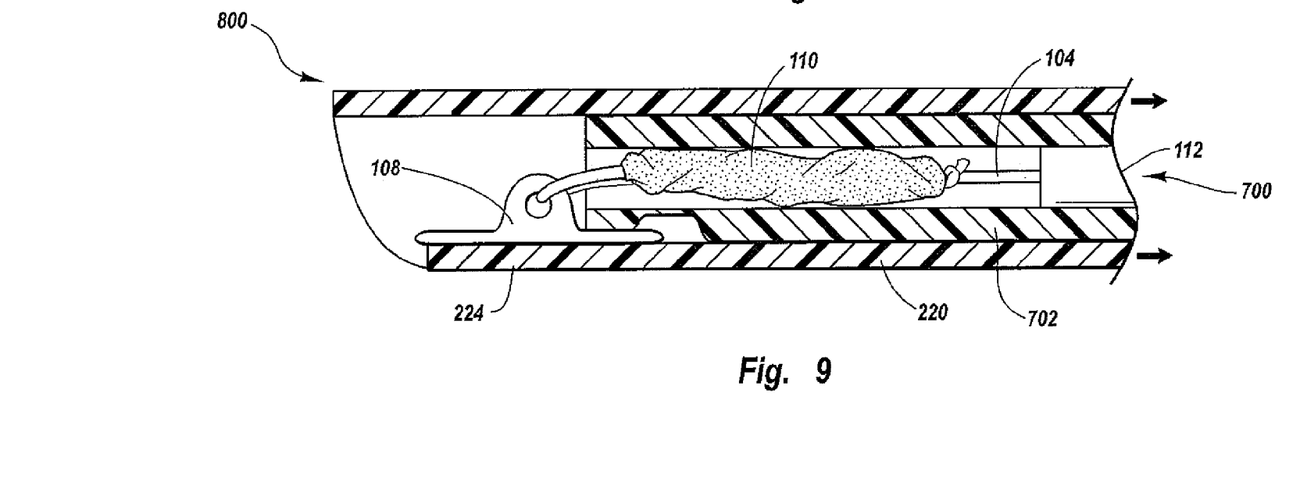
FIG. 9 is a cross-sectional view of the tissue puncture closure device of FIG. 7 shown in relation to the insertion sheath of FIG. 8 in a second position according to one embodiment of the present invention.
Figure 10:
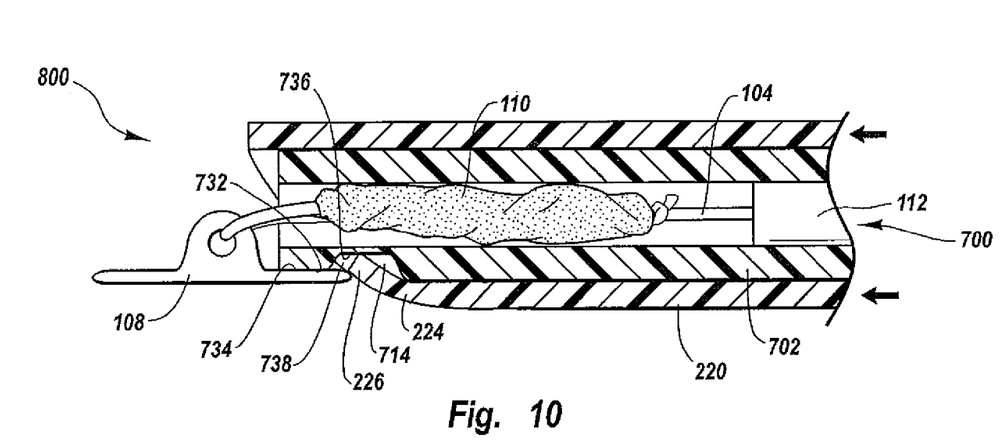
FIG. 10 is a cross-sectional view of the tissue puncture closure device of FIG. 7 shown in relation to the insertion sheath of FIG. 8 in a third position according to one embodiment of the present invention.
Figure 11:
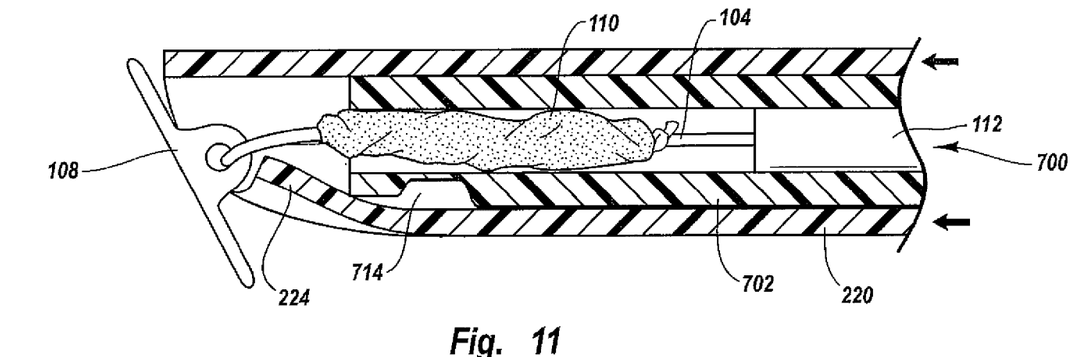
FIG. 11 is a cross-sectional view of the tissue puncture closure device of FIG. 7 shown in relation to the insertion sheath of FIG. 8 in a fourth position according to one embodiment of the present invention.

Referring next to FIGS. 8-9, a tissue closure assembly 800 includes the tissue closure device 700 and the insertion sheath 220. As the closure device 700 is inserted through the insertion sheath 220, the anchor 108 impinges and deforms the monofold 224 in a manner similar to that described above with reference to FIG. 3. However, as the anchor passes out of the insertion sheath 220 as shown in FIG. 10, the monofold 224 springs back and impinges on the second surface 736 spaced from the first surface 734 of the anchor 108 instead of the first surface 732 that the anchor 108 bears against. Accordingly, as the tissue closure device 700 is pulled back into the insertion sheath 220, the tip 226 of the monofold slips easily into the gap 738, advantageously reducing or eliminating any possibility of the anchor 108 sliding back into the insertion sheath 220. Therefore, as the closure device 700 is pulled proximally with respect to the insertion sheath 220, the anchor rotates and deploys as shown in FIG. 11.

Figure 12:
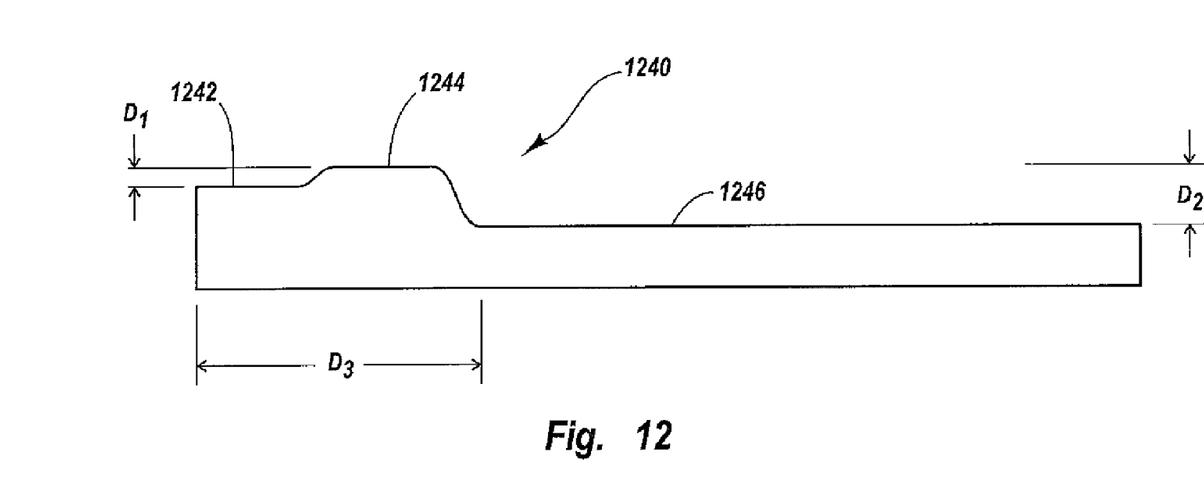
FIG. 12 is a side view of a die component of a tissue puncture closure assembly according to one embodiment of the present invention.

The multi-level nest 714 may be created, for example, by heating and/or compressing or crushing the first end 706 of the carrier tube 702 with a die, such as the anvil 1240 shown in FIG. 12. Therefore, the anvil 1240 may also be part of the tissue closure assembly 800. The anvil 1240 is made of structural materials such as steel and may include a first level 1242 and a second level 1244. According to the embodiment of FIG. 12, the second level 1244 is higher than the first level 1242 by a predetermined distance D1. D1 may range between approximately 0.01 and 0.030 inches, preferably about 0.020 inches. The first and second levels 1242, 1244 are each higher than a main level 1246 and correspond to compression zones in the carrier tube 702 (FIG. 7) that result in the first and second surfaces 732, 736 (FIG. 7) of the nest 714 (FIG. 7). The second level 1244 is higher than the main level 1246. Normally, the main level 1246 does not crush or impinge on the carrier tub 702 (FIG. 7), but instead limits the compression caused by the first and second levels 1242, 1244. The first level 1242 is offset from the second level 1244 by a second distance D2. D2 may range between approximately 0.030 and 0.080 inches, preferably about 0.055 inches. Other methods of creating the nest 714 (FIG. 7) may also be used.

The present invention is not limited to the split-level configuration for the nest 714 as shown in FIG. 7. For example, according to FIG. 13 there is another tissue puncture closure device 1300 shown. The tissue puncture closure device 1300 includes a carrier tube 1302 with a multi-level nest 1314 comprising three spaced surfaces 1332, 1336, 1337, respectively, that are generally parallel with one another. The three spaced surfaces 1332, 1336, 1337 create a tiered gap 1338 may include first and second gaps 1339 and 1341, and may even further ensure that the monofold 224 (FIG. 2B) or other one-way valve will not allow the anchor 108 to reenter the insertion sheath 220 (FIG. 2B) once it has passed therethrough. Other multi-level nests may also be used to create more than three surfaces, if desired.

Figure 13:
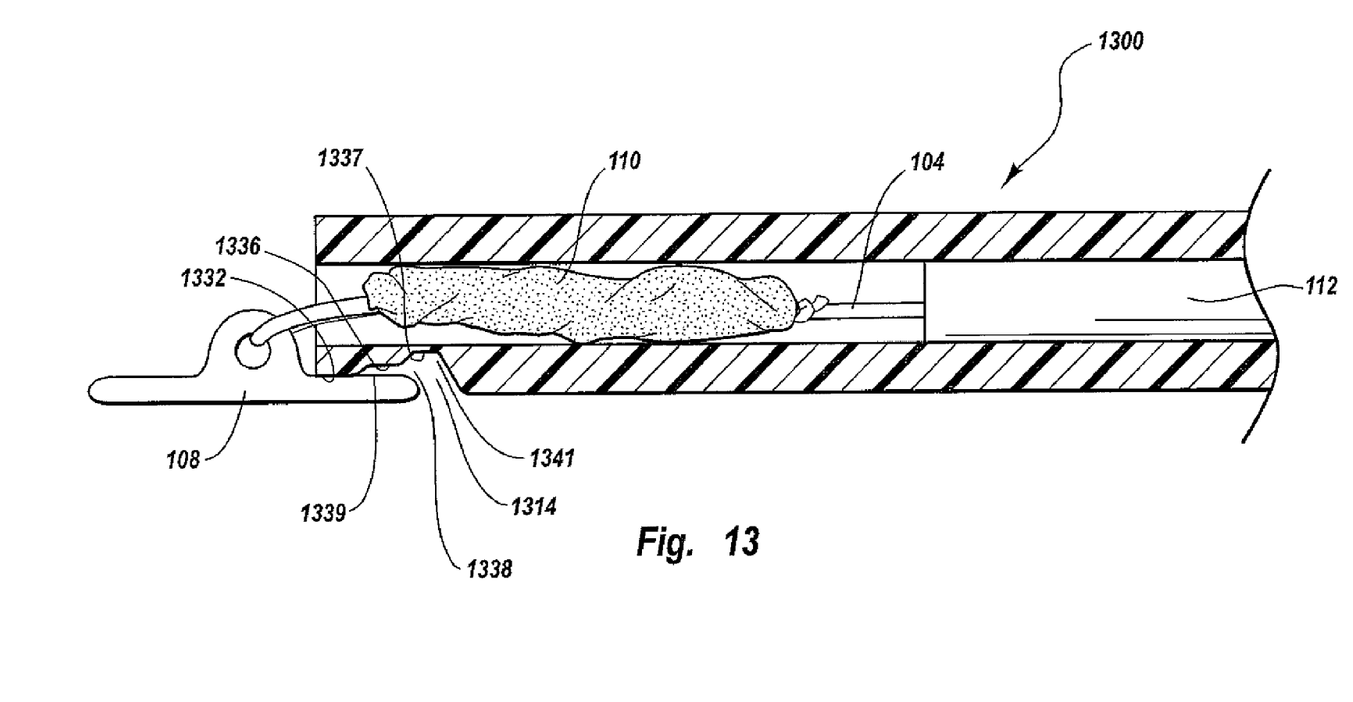
FIG. 13 is a cross-sectional view of a tissue puncture closure device according to another embodiment of the present invention.
Figure 14:
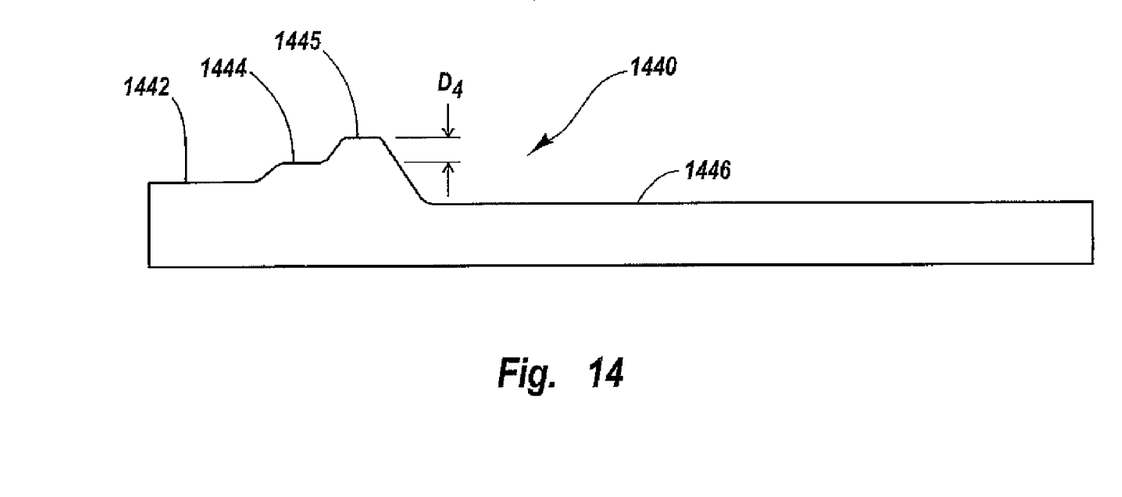
FIG. 14 is a side view of another die component of a tissue puncture closure assembly according to one embodiment of the present invention.
Figure 15:
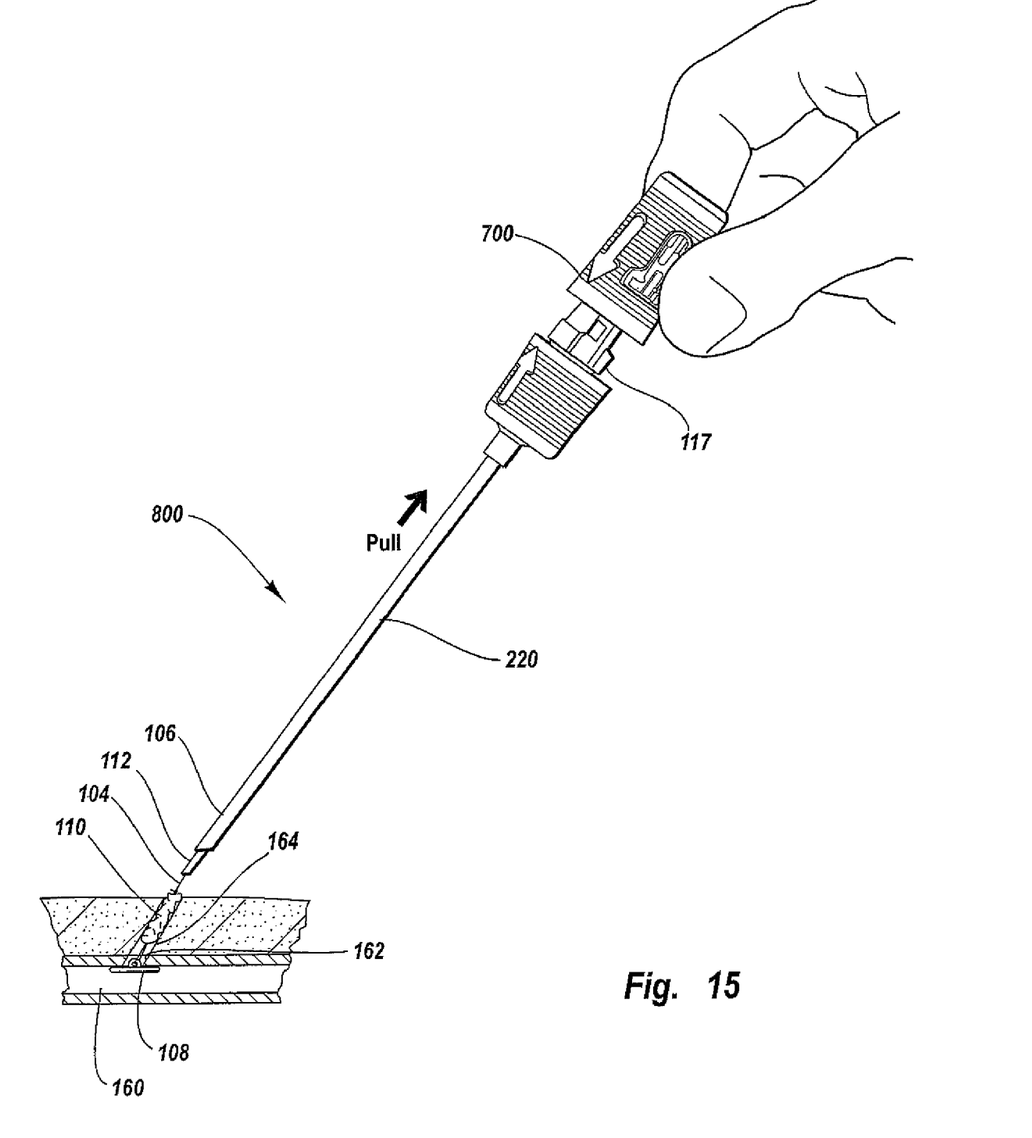
FIG. 15 is a perspective view of the tissue puncture closure device of FIG. 7 or 13 and the insertion sheath of FIG. 8 shown in relation to a patient with an anchor deployed according to the present invention.

The multi-level nest 1314 may be formed by heating and/or compressing the carrier tube (not shown in FIG. 13) with a die, such as the anvil 1440 shown in FIG. 14. Therefore, the anvil 1440 may also be part of the tissue closure assembly 800 (FIG. 15). According to the embodiment of FIG. 14, the anvil 1440 includes a first level 1442, a second level 1444, and a third level 1445. The second level 1444 is higher than the first level 1442, and the third level 1445 is higher than the second level 1444. All three levels 1442, 1444, 1445 are higher than a main level 1446 and correspond to the first, second and third surfaces or compression zones 1332, 1336, 1337, respectively, of the carrier tube (not shown in FIG. 13).

The embodiments shown in FIGS. 8 and 13 may include similar or identical elements shown in FIGS. 1-2. For example, referring to FIG. 15, the closure device 800 (and 1300 in FIG. 13) may include the suture 104 (or other filament) extending from the first end 106 of the closure device 800, a sealing plug such as the collagen sponge 110 slidingly attached to the suture 104 and the tamping tube 112. FIG. 15 shows the closure device 800 inserted partially through a puncture 162 in an artery 160, with the anchor 108 and the collagen sponge 110 deployed.

Figure 16:
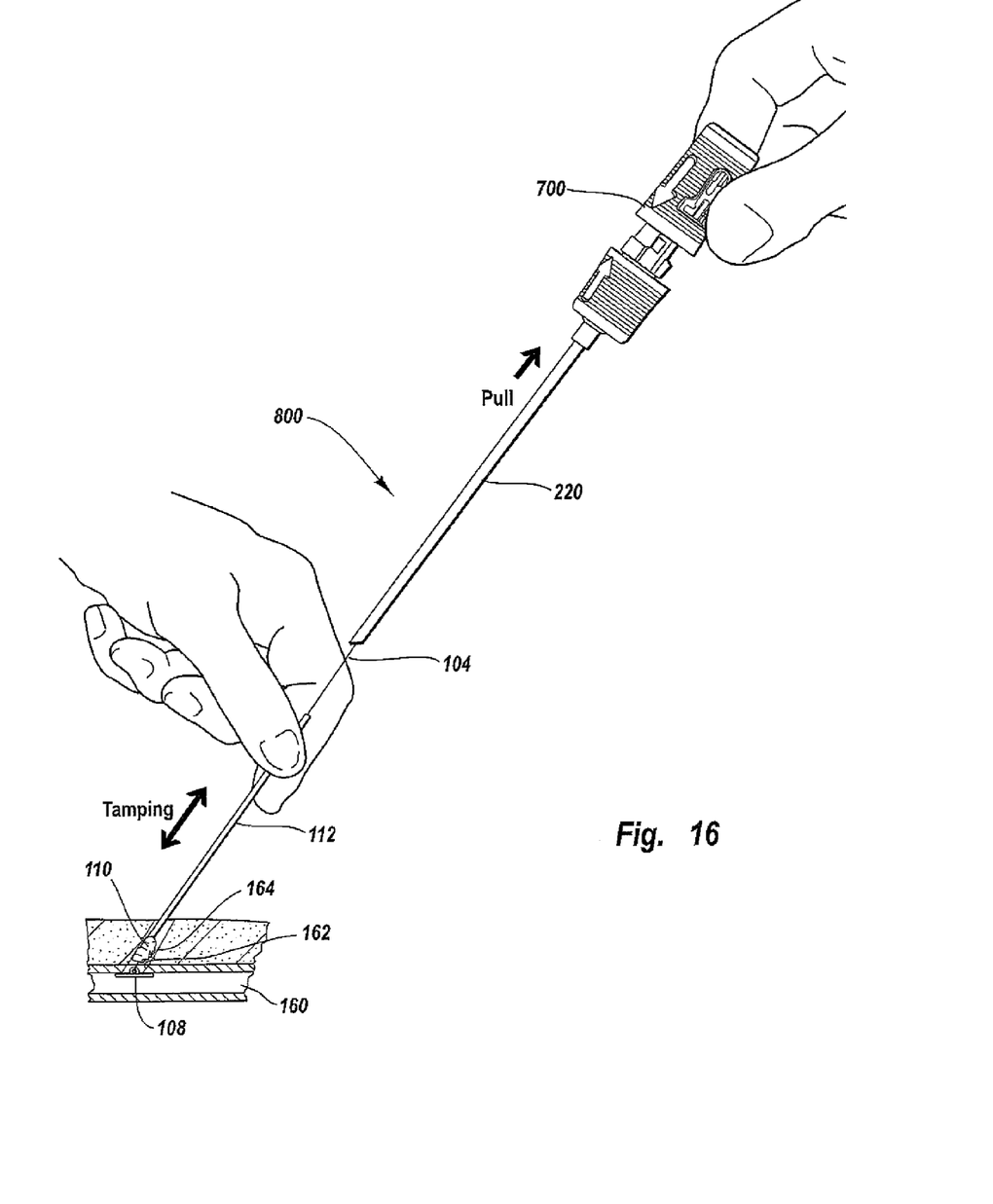
FIG. 16 is a perspective view according to FIG. 15 with an operator tamping a sealing plug according to the present invention.

Referring to FIGS. 15-16, a method of sealing the puncture 160 according to the present invention may include inserting the tissue puncture closure device 800 into a percutaneous incision 164 and deploying the anchor 108 into the tissue puncture 162 as shown in FIG. 15. The method may also include withdrawing the closure device 800 from the percutaneous incision 164 and tamping the sealing plug 110 toward the anchor 108 with the tamping tube 112. The step of deploying the anchor may further comprise sliding the monofold tip 226 (FIGS. 3-4) of the insertion sheath 220 into the gap 738 (FIG. 7) formed between the anchor 108 and the multi-level nest 714 (FIG. 7) disposed in the carrier tube 702.

While the invention has been particularly shown and described with reference to embodiments thereof, it will be understood by those skilled in the art that various other changes in the form and details may be made without departing from the scope of the invention.

We claim:

1. A tissue puncture closure assembly comprising a closure device for partial insertion into and sealing of an internal tissue wall puncture, the closure device comprising:
   a filament extending from a first end of the closure device;
   a nest comprising first and second surfaces each facing in a radially outward direction, the first surface being positioned proximal of the second surface;
   an anchor for insertion through the tissue wall puncture seated in the nest and attached to the filament at the first end of the closure device, the anchor having a first surface facing the first surface of the nest in a radially inward direction and in contact with the second surface of the nest;
   a sealing plug slidingly attached to the filament adjacent to the anchor;
   a gap between the first surface of the nest and the first surface of the anchor.

2. A tissue puncture closure assembly comprising a closure device for partial insertion into and sealing of an internal tissue wall puncture according to claim 1 wherein the first and second nest surfaces are approximately parallel to one another.

3. A tissue puncture closure assembly comprising a closure device for partial insertion into and sealing of an internal tissue wall puncture according to claim 1, further comprising a carrier tube, wherein the first nest surface comprises a first portion of the carrier tube compressed to a first depth, and the second nest surface comprises a second portion of the carrier tube compressed to a second depth.

4. A tissue puncture closure assembly comprising a closure device for partial insertion into and sealing of an internal tissue wall puncture according to claim 3 wherein the first depth is deeper than the second depth.

5. A tissue puncture closure assembly comprising a closure device for partial insertion into and sealing of an internal tissue wall puncture according to claim 3, further comprising a third nest surface, wherein the third nest surface comprises a third portion of the carrier tube compressed to a third depth.

6. A tissue puncture closure assembly comprising a closure device for partial insertion into and sealing of an internal tissue wall puncture according to claim 5 wherein the third depth is deeper than the first depth and the second depth.

7. A tissue puncture closure assembly comprising a closure device for partial insertion into and sealing of an internal tissue wall puncture according to claim 1, further comprising an insertion sheath receptive of the closure device and having a first end.

8. A tissue puncture closure assembly comprising a closure device for partial insertion into and sealing of an internal tissue wall puncture according to claim 7 wherein the first end comprises a monofold.

9. A tissue puncture closure assembly comprising a closure device for partial insertion into and sealing of an internal tissue wall puncture according to claim 8 wherein the monofold fits in the gap between the nest and the anchor upon distal movement of the insertion sheath relative to the closure device.

10. A tissue puncture closure assembly comprising a closure device for partial insertion into and sealing of an internal tissue wall puncture according to claim 1, further comprising a bypass tube initially disposed about the anchor to temporarily hold the anchor in the nest.

11. A tissue puncture closure assembly comprising a closure device for partial insertion into and sealing of an internal tissue wall puncture, the closure device comprising:
   a carrier tube having a split-level nest at a distal end, the split-level nest having first and second surfaces facing radially outward, the first surface being spaced proximal of the second surface;
   a filament extending at least partially through the carrier tube;
   an anchor attached to the filament at the distal end of the carrier tube and seated in the split-level nest, the anchor having a first surface facing radially inward and arranged contacting the second surface of the split-level nest and spaced apart from the first surface of the split-level nest.

12. A tissue puncture closure assembly comprising a closure device for partial insertion into and sealing of an internal tissue wall puncture according to claim 11, further comprising a sealing plug disposed inside the distal end of the carrier tube.

13. A tissue puncture closure assembly comprising a closure device for partial insertion into and sealing of an internal tissue wall puncture according to claim 12 wherein the sealing plug is slidingly attached to the filament.

14. A tissue puncture closure assembly comprising a closure device for partial insertion into and sealing of an internal tissue wall puncture according to claim 11 wherein the spacing between the first surface of the anchor and the second surface of the split-level nest defines a gap between the split-level nest and the anchor.

15. A tissue puncture closure assembly comprising a closure device for partial insertion into and sealing of an internal tissue wall puncture according to claim 14, further comprising an insertion sheath receptive of the closure device and having a first end.

16. A tissue puncture closure assembly comprising a closure device for partial insertion into and sealing of an internal tissue wall puncture according to claim 15 wherein the first end comprises a monofold in the insertion sheath.

17. A tissue puncture closure assembly comprising a closure device for partial insertion into and sealing of an internal tissue wall puncture according to claim 16 wherein the monofold fits in the gap between the first and second surfaces of the split-level nest upon distal movement of the insertion sheath relative to the closure device.

18. A tissue puncture closure assembly comprising a closure device for partial insertion into and sealing of an internal tissue wall puncture according to claim 11 wherein the split-level nest comprises a first portion of the carrier tube compressed to a first depth, and the second nest surface comprises a second portion of the carrier tube compressed to a second depth.

19. A tissue puncture closure assembly comprising a closure device for partial insertion into and sealing of an internal tissue wall puncture according to claim 11, wherein the split-level nest further comprises a tri-level nest, each level of the tri-level nest facing radially outward.

20. A tissue puncture closure device, comprising:
a carrier tube having a distal end;
a sealing plug disposed inside the distal end of the carrier tube;
a multi-level compression zone disposed in the distal end of the carrier tube and having first and second compression zone surfaces each facing radially outward, the first compression zone surface being positioned proximal of the second compression zone surface;
an anchor seated in the multi-level compression zone of the carrier tube and having a first surface facing and in contact with the second compression zone surface and spaced apart from the first compression zone surface.

21. A tissue puncture closure device according to claim 20 wherein a first gap is formed between the anchor and the first compression zone surface.

22. A tissue puncture closure device according to claim 21 wherein the multi-level compression zone further comprises a third compression zone surface, wherein a second gap larger than the first gap is formed between the anchor and the third compression zone surface.

23. A tissue puncture closure device according to claim 20, further comprising a filament extending through the carrier tube, wherein the filament is threaded through the sealing plug and the anchor.

24. A tissue puncture closure device assembly comprising:
a carrier tube having a distal end and a filament extending therethrough;
a sealing plug disposed inside the distal end of the carrier tube and attached to the filament;
an anchor attached to the filament at the distal end of the carrier tube, the anchor including a radially inward facing surface;
a multi-level die for compressing a multi-level nest in the distal end of the carrier tube, the multi-level die including at least first and second radially facing surfaces that form first and second radially outward facing surfaces of the multi-level nest that face the radially inward facing surface of the anchor, the second radially facing surface arranged to form the second radially outward facing surface of the multi-level nest distal of the first radially outward facing surface of the multi-level nest and arranged to contact the radially inward facing surface of the anchor, and the first radially facing surface arranged to form the first radially outward facing surface of the multi-level nest spaced apart from the radially inward facing surface of the anchor.

25. A tissue puncture closure device assembly according to claim 24 wherein the multi-level die further comprises a third level radially facing surface, the third radially facing surface being lower than the first and second radially facing surfaces.

26. A method of making a tissue puncture closure device, comprising:
providing a carrier tube;
threading a suture through the carrier tube;
threading the suture through a sealing plug and an anchor;
compressing a multi-level nest into a distal end of the carrier tube, the multi-level nest including at least first and second radially outward facing nest surfaces, the first radially outward facing nest surface being spaced proximal of the second radially outward facing nest surface;
nesting the anchor in the multi-level nest with a radially inward facing surface of the anchor facing and in contact with the first radially outward facing nest surface, and facing and spaced apart from the second radially outward facing nest surface.

27. A method of making a tissue puncture closure device according to claim 26 wherein nesting the anchor in the multi-level nest further comprises leaving a gap between a portion of the anchor and one level of the multi-level nest.

28. A method of making a tissue puncture closure device according to claim 26 wherein compressing comprises engaging a multi-level die with the distal end of the carrier tube.

29. A method of making a tissue puncture closure device according to claim 26 wherein the multi-level nest comprises two or three different levels, each different level including a radially outward facing surface.

30. A tissue puncture closure device made according to the method of claim 26.

* * * * *